US011845774B2

(12) United States Patent
Duan et al.

(10) Patent No.: US 11,845,774 B2
(45) Date of Patent: *Dec. 19, 2023

(54) STEROL DERIVATIVES AND PREPARATION METHOD AND USES THEREOF

(71) Applicant: BEIJING PEKING UNIVERSITY WBL BIOTECH CO., LTD., Beijing (CN)

(72) Inventors: Zhenwen Duan, Beijing (CN); Shuren Guo, Beijing (CN); Xuemei Li, Beijing (CN)

(73) Assignee: Beijing Peking University WBL Biotech Co., Ltd., Beijing (CN)

(*) Notice: Subject to any disclaimer, the term of this patent is extended or adjusted under 35 U.S.C. 154(b) by 0 days.

This patent is subject to a terminal disclaimer.

(21) Appl. No.: 17/818,302

(22) Filed: Aug. 8, 2022

(65) Prior Publication Data

US 2022/0387453 A1  Dec. 8, 2022

Related U.S. Application Data

(62) Division of application No. 17/071,963, filed on Oct. 15, 2020, now Pat. No. 11,634,454, which is a
(Continued)

(30) Foreign Application Priority Data

Dec. 26, 2011  (CN) .......................... 201110441993.2
Dec. 26, 2011  (CN) .......................... 201110442009.4
Jan. 18, 2012  (CN) .......................... 201210015475.9

(51) Int. Cl.
*A61K 36/06* (2006.01)
*C07J 71/00* (2006.01)
(Continued)

(52) U.S. Cl.
CPC ........... *C07J 71/0005* (2013.01); *A61K 31/58* (2013.01); *A61K 36/06* (2013.01); *A61K 36/899* (2013.01); *A61P 35/00* (2018.01); *A61K 2236/00* (2013.01)

(58) Field of Classification Search
CPC ......... A61K 36/06; A61P 3/00; C07J 71/0005
See application file for complete search history.

(56) References Cited

U.S. PATENT DOCUMENTS 6,020,383 A   2/2000  Stone et al.
6,046,022 A   4/2000  Zhang et al.
(Continued)

FOREIGN PATENT DOCUMENTS

CN   1982327 A    6/2007
CN   101104003 A  1/2008
(Continued)

OTHER PUBLICATIONS

Hong et al., Anti-Cancer Effects of Chinese Red Yeast Rice beyond Monacolin K alone in Colon Cancer Cells, J Nutr Biochem. Jul. 2008; 19(7): 448-458.*
(Continued)

*Primary Examiner* — Svetlana M Ivanova
(74) *Attorney, Agent, or Firm* — Seed IP Law Group LLP

(57) ABSTRACT

The present invention pertains to pharmaceutical chemical field, and relates to a sterol derivative as well as preparation method and uses thereof. Specifically, the present invention relates to a compound of Formula I, or a pharmaceutically acceptable salt, ester or ether thereof, wherein, $R_1$ is selected from the group consisting of —OH, =O(carbonyl), H, and $C_1$-$C_3$ alkyl; $R_2$ is selected from the group consisting of —OH, H, and $C_1$-$C_3$ alkyl; $R_3$ is selected from the group consisting of —OH, =O, H, and $C_1$-$C_3$ alkyl; $R_4$ is selected
(Continued)

from the group consisting of —OH, H, and $C_1$-$C_3$ alkyl; and none, one, two, three or four of $R_1$, $R_2$, $R_3$, and $R_4$ are —OH. The compound of the present invention can inhibit HMG-CoA reductase, tumor cells and lipase effectively, and is a potential drug for reducing blood-fat, antitumors, or for losing weight.

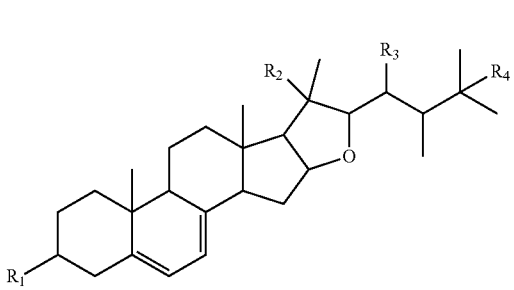

I

4 Claims, 3 Drawing Sheets

Related U.S. Application Data division of application No. 14/368,494, filed as application No. PCT/CN2012/087360 on Dec. 25, 2012, now Pat. No. 10,889,612.

(51) Int. Cl.
| | | |
|---|---|---|
| A61K 36/899 | (2006.01) | |
| A61P 35/00 | (2006.01) | |
| A61K 31/58 | (2006.01) | |

(56) References Cited

U.S. PATENT DOCUMENTS

| | | |
|---|---|---|
| 6,495,173 B1 | 12/2002 | Yegorova |
| 6,541,005 B1 | 4/2003 | Yegorova |
| 6,541,006 B1 | 4/2003 | Yegorova |
| 6,544,525 B1 | 4/2003 | Yegorova |
| 6,576,242 B1 | 6/2003 | Yegorova |
| 7,238,348 B2 | 7/2007 | Liang et al. |
| 9,371,304 B2 | 6/2016 | Duan et al. |
| 10,093,695 B2 | 10/2018 | Duan et al. |
| 10,099,998 B2 | 10/2018 | Duan et al. |
| 11,634,454 B2 * | 4/2023 | Duan ............... A61K 31/58 514/172 |
| 2009/0004290 A1 | 1/2009 | Voelker |
| 2009/0263453 A1 | 10/2009 | McKay et al. |
| 2015/0025130 A1 | 1/2015 | Duan et al. |
| 2015/0031657 A1 | 1/2015 | Duan et al. |
| 2018/0022688 A1 | 1/2018 | Duan et al. |

FOREIGN PATENT DOCUMENTS

| | | |
|---|---|---|
| CN | 101313919 A | 12/2008 |
| CN | 101469014 A | 7/2009 |
| CN | 101942003 A | 1/2011 |
| CN | 103172693 A | 6/2013 |
| WO | WO 9814177 A1 | 4/1998 |
| WO | WO 2011003284 A1 | 1/2011 |

OTHER PUBLICATIONS

Ye et al., "Potential Protective Effect of Long-Term Therapy with Xuezhikang on Left Ventricular Diastolic Function in Patients with Essential Hypertension," The Journal of Alternative and complementary Medicine, vol. 15, No. 7, 2009, pp. 719-725.
International Preliminary Report on Patentability (PCT Chapter I) corresponding to International Patent Application No. PCT/CN2012/087360 dated Jul. 1, 2014, 10 pages.
Chen et al., "Polyhydroxylated steroids from the octocoral Isis hippuris," Tetrahedron, 2011, vol. 67, pp. 8116-8119.
Duan et al., "New 3,16,20,22,23,25-hexahydroxy-ergosterol useful in composition for inhibiting 3-hydroxy-3-methylglutarylcoenzymeA," WPI/Thomson (abstract), Jan. 2011, vol. 2011, No. 9, abstract.
Goyot et al., "Effect of Endoperoxides from Marine Origin on 3-Hydroxy-3-methylglutaryl-COA Reductase (HMGR) Activity of Infant Skin Fibroblasts in Culture," Biomedicine & Pharmacotherapy, 1986, vol. 40, pp. 195-197.
Jeon et al., "Red yeast rice extracts suppress adipogenesis by down-regulating adipogenic transcription factors and gene expression in 3T3-L1 Cells," Life Sciences, 2004, vol. 75, pp. 3195-3203.
Kim et al., "Development of lipase inhibitors from various derivatives of monascus pigment produced by Monascus fermentation," Food Chemistry, 2007, vol. 101, pp. 357-364.
Ma et al., "Synthesis of glycosides bearing the disaccharide of OSW-1 or its 1--->4-linked analogue and their antitumor activities," Carbohydrate Research, 2000, vol. 329, pp. 495-505.
Shang et al., "Cytotoxic steroids from Monascus purpureusfremented rice," Steroids, 2011, vol. 76, pp. 1185-1189.
Database accession No. EMB-2006270002, Wang, "Xuezhikang capsule for hyperlipidemia: A systematic review," May 2006.
Ye et al., "Effect of xuezhikang on al- and 132-microglobulin in patients with essential hypertension," Journal of Human Hypertension, 2009 (published online 2008), vol. 23, pp. 72-74.
European Search Report, dated Jun. 1, 2015, EP application No. 12862540.7, 17 pages.
Office Action (Written Opinion), dated Mar. 26, 2015, SG Application No. 11201403618P, 13 pages.
International Search Report (English Translation) corresponding to PCT/CN2012/087360 dated Apr. 4, 2013; 4 pages.
Written Opinion, dated Apr. 4, 2013, PCT Application No. PCT/CN2012/087360, 9 pages.
Office Action (Chinese version; non-English) with search result issued in corresponding priority Application No. 201110442009.4 citing CN1982327, 5 pages.
Shi et al., "The Efficacy of Xuezhikang on Hyperlipidemia and its Influence to BMI," Capital Medicine, 1997, No. 11, pp. 33-34.
Xie et al., "Effect of Xuezhikang on diabetic patients complicated with hyperlipidemia (with 60 cases)," China Tropical Medicine, vol. 10, No. 7, Jul. 2010, p. 859.
Lin et al., "A Meta-analysis on lipid-regulation effect of Xuezhikang in patients with coronary heart disease complicating hyperlipemia," Chinese Journal of Evidence-Based Cardiovascular Medicine, Feb. 2014, vol. 6, No. 1, pp. 25-30.
Hanai et al., The muscle-specific ubiquitin ligase atrogin-1/MAFbx mediates statin-induced muscle toxicity, The Journal of Clinical Investigation, vol. 117, No. 12, 3940-3951, Dec. 2007 (Year: 2007).
Guarino, The molecular design of prodrugs by functional group, Prodrugs and Targeted Delivery: Towards Better ADME Properties, 31-60, 2011 (Year: 2011).
Parrott et al., Incorporation and controlled release of silyl ether prod rugs from PRINT nanoparticles, Journal of the American Chemical Society, vol. 134, 7978-7982, Apr. 23, 2012 (Year: 2012).
Davies et al., Protection of hydroxy groups by silylation: Use in peptide synthesis ans as lipophilicity modifiers for peptides, Journal of the Chemical Society, Perkin Transactions 1, 3043-3048, 1992 (Year: 1992).
Lu et al., "Effect of Xuezhikang, an Extract from Red Yeast Chinese Rice, on Coronary Events in a Chinese Population with Previous Myocardial Infarction," Am J Cardiol 101: 1689-1693, 2008.
Klimek et al., "(Safety and efficacy of red yeast rice (*Monascus purpureus*) as an alternative therapy for hyperlipidemia," P T. Jun. 2009;34(6):313-27. PMID: 19572049; PMCID: PMC2697909. PT. Jun. 2009; 34(6): 313-327.).

(56) References Cited

OTHER PUBLICATIONS

Wei et al., "Hypolipidemic and anti-atherogenic effects of long-term Cholestin (*Monascus purpureus*-fermented rice, red yeast rice) in cholesterol fed rabbits," J Nutr Biochem, Jun. 2003; 14(6):314-8. doi: 10.1016/s0955-2863(03)00051-2. PMID: 12873712.

* cited by examiner

STEROL DERIVATIVES AND PREPARATION METHOD AND USES THEREOF

This application is a divisional application of U.S. patent application Ser. No. 17/071,963, filed Oct. 15, 2020, which is a divisional application of U.S. patent application Ser. No. 14/368,494, filed Jun. 24, 2014, issued as U.S. Pat. No. 10,889,612, which is a 371 national stage application of International Patent Application No. PCT/CN2012/087360, filed Dec. 25, 2012, which claims the benefit of Chinese Patent Application No. 201110441993.2, filed Dec. 26, 2011, and Chinese Patent Application No. 201110442009.4, filed Dec. 26, 2011, and Chinese Patent Application No. 201210015475.9, filed Jan. 18, 2012, which applications are incorporated herein by reference in their entirety.

TECHNICAL FIELD

The present invention pertains to pharmaceutical chemical field, and relates to a sterol derivative as well as preparation method and uses thereof.

BACKGROUND ART

*Monascus*-fermented rice is a purple red rice koji prepared by using rice as raw material via fermentation with *Monascus*. *Monascus*-fermented rice is also called Danqu (丹曲) in ancient China, which is obtained via fermentation in which koji or mold culture with *Monascus* as main component is cultured on cooked rice; it is red color, and thus is also called as red koji, red rice, or red wine dreg; and it is also called Fujian koji, Fujian rice, etc., because it is primarily produced in Fujian.

China has a long history of utilizing *Monascus*, and it has been used for koji making since Han Dynasty. *Monascus*-fermented rice is a traditional Chinese medicine as both food and drug. It had been widely used for food coloring, winemaking, fermentation, Chinese medicine as early as in ancient times. <Principle of Correct Diet> (《饮膳正要》) has the recordation that *Monascus*-fermented rice is of "sweet taste and neutral nature and smooth in taste, non-toxic" and "invigorating spleen, supplementing Qi, warming spleen and stomach"; <Compendium of Materia Medica> (《本草纲目》) has the recordation of "sweet, warm, non-toxic" "capable of treating dysmenorrheal, extravasated blood after delivery, by grinding with rice wine and then drinking"; <Addendum for Amplification on Materia Medica> (《本草衍义补遗》) has recordation of "activating blood, helping digestion, invigorating spleen and warming stomach, capable of treating red and white vaginal discharge and diarrhea, as well as traumatic injury".

Since 1970s, when Prof. Endo of Japan firstly separated from red *Monascus* (*Monascus ruber*) a physiologically active substance, monacolin K, many researchers home and abroad discovered continually from *Monascus* metabolite other physiologically active substances, including monacolin compounds, *Monascus* pigment, pressure releasing component GABA and antioxidant component dimerumic acid, and some terpenoids being separated recently. With the development of modern biochemistry and pharmacology, functions of *Monascus*-fermented rice such as hypolipemic, lowering blood pressure, hyperglycemic, anti-obesity, anti-cancer, prophylaxis and treatment of senile dementia and osteoporosis are continuously revealed, which add more connotations to traditional *Monascus*-fermented rice.

"Xuezhikang" capsules are an efficient, safe and modern Chinese medicine for lipid regulation which is prepared by *Monascus* fermentation and developed by Beijing Peking University WBL Biotechnology Co., Ltd. It is useful in treatment of indications such as cardiovascular and cerebrovascular diseases caused by hyperlipemia and atherosclerosis. Its action mechanism is of inhibiting endogenous cholesterol synthesis, reducing serum total cholesterol (TC), blood triglyceride (TG), low density lipoprotein (LDL) and elevating high density lipoprotein (HDL) level via inhibiting 3-hydroxy-3-methyl-glutaryl coenzyme A (HMG-CoA). Xuezhikang capsules are of an alcohol extract of *Monascus*-fermented rice, which are rich in a series of natural statins. Besides statins, Xuezhikang capsules further contain pigment, isoflavone, sterol, 20 kinds of amino acids, unsaturated fatty acids, and many trace elements. Thus, it is still in need to find novel compounds capable of lowering lipid or inhibiting HMG-CoA reductase activity.

In addition, Xuezhikang may further comprise some unknown anticancer ingredients. Thus, it is also in need to find novel anticancer compounds.

Obesity is a universal internal secretion metabolic disease, and intends to be wide-spread worldwide. It not only affects posture and activity, but also is closely associated with hyperlipemia, atherosclerosis, coronary heart disease, diabetes and so on. The occurrence of obesity relates to many factors, such as genetic factors, environmental factors, dietary habits, among which high fat diet is an important factor of obesity. In recent years, drug therapy is an effective means for treatment of obesity, which its therapeutic goal is usually achieved by reducing fat absorption. Lipases of pancreas and stomach are necessary for digestion and absorption of fats in intestinal tract. After fats in food are hydrolyzed into monoacylglycerol and free fatty acid, they are absorbed in intestinal tract, and then fats are synthesized again in vivo, causing fat accumulation, and finally resulting in obesity. Using lipase inhibitors can effectively inhibit decomposition and catalysis effects of lipases on fats in intestinal tract, so as to achieve the goal of reduction of fat absorption, control and treatment of obesity (CHEN Jin, etc., Advances in studying drug therapy of obesity, Chinese Archives of Traditional Chinese Medicine, 2007, 25(5):947-948; WU Jing, etc., Advances in drug therapy of obesity, Medical Recapitulate, 2006, 12(11):693-693).

At present, only 2 drugs have been approved by FDA of US for long-term treatment of obesity: sibutramin (weight-reducing aid acting on central nervous) and orlistat (lipase inhibitor in gastrointestinal tract). However, both of the two drugs have significant adverse reactions: sibutramin has side-effects mainly including thirst, astriction, dizziness and insomnia, while orlistat has adverse reactions mainly including gastrointestinal symptoms, such as diarrhea, bellyache, oily flecks, flatulence, etc., and their long-term effects should be further evaluated.

Thus, it is still in need at present to find novel drugs having function of inhibiting lipase.

CONTENTS OF THE INVENTION

With a lot of experiments and inventive work, the inventors of the present invention obtain a new sterol derivative, and the inventors surprisingly find the compound of the present invention can effectively inhibit HMG-CoA reductase, and thus is a potential drug for reduction or regulation of blood-fat or prophylaxis and/or treatment of dyslipidemia, hyperlipemia, hypercholesterolemia, or atherosclerotic. In addition, the inventors further surprisingly find that: 1) the compound of the present invention can effectively inhibit proliferation of cancer cells (tumor cells), and is a potential drug for prophylaxis and/or treatment and/or adjunctive treatment of cancers; 2) the compound of the present invention can effectively inhibit activity of lipase, and thus is a potential drug for prophylaxis and/or treatment and/or adjunctive treatment of obesity or diseases associated with obesity. Thus, the following inventions are provided.

One aspect of the present invention relates to a compound of Formula I, or a pharmaceutically acceptable salt, ester or ether thereof,

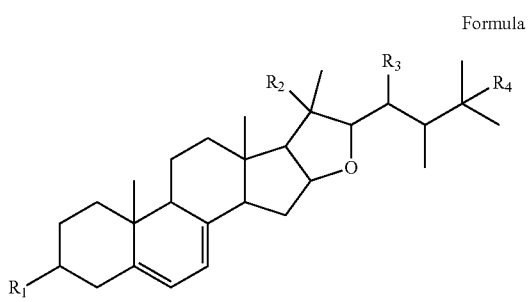

Formula I wherein, $R_1$ is selected from the group consisting of —OH, =O (carbonyl), H, and $C_1$-$C_3$ alkyl;

$R_2$ is selected from the group consisting of —OH, H, and $C_1$-$C_3$ alkyl;

$R_3$ is selected from the group consisting of —OH, =O, H, and $C_1$-$C_3$ alkyl;

$R_4$ is selected from the group consisting of —OH, H, and $C_1$-$C_3$ alkyl;

and none, one, two, three or four of $R_1$, $R_2$, $R_3$, and $R_4$ are —OH.

As for the ester or ether of compound of Formula I, sites for forming the ester or ether are none, one, two, three or four of $R_1$, $R_2$, $R_3$, and $R_4$.

In one embodiment of the present invention, $R_1$ is —OH or =O (carbonyl), $R_2$, $R_3$ and $R_4$ are all H.

The compound or pharmaceutically acceptable salt, ester or ether of any one of items of the present invention, it is a compound of Formula II as follows, or a pharmaceutically acceptable salt, ester or ether thereof,

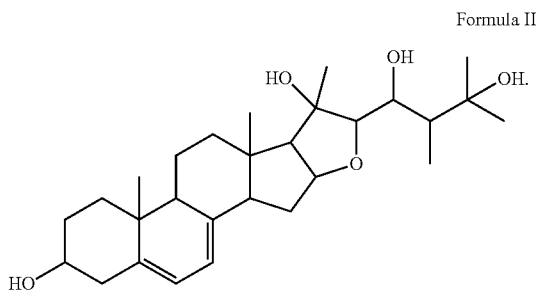 [SMILES: CC(C(O)C1OC2CC3C4=CC=C5CC(O)CCC5(C)C4CCC3(C)C2C1(C)O)C(C)(C)O]

Formula II

The compound of Formula II has chemical name of: 16,22-epoxy-ergosta-5,7-dien-3,20,23, 25-tetraol.

In the compound or pharmaceutically acceptable salt, ester or ether of any one of items of the present invention, said ester is selected from the group consisting of formate, acetate, propionate and sulfonate; said ether is tert-butyl-dimethyl silyl ether; specifically, said sulfonate group is p-tolylsulfonate or trifluoromethylsulfonate.

The present invention further relates to a hydrate or solvate of the compound of Formula I or the compound of Formula II.

Another aspect of the present invention relates to a method for preparing the compound of Formula I or the compound of Formula II, comprising the following steps:

1) providing *Monascus*-fermented rice and/or alcohol extract of *Monascus*-fermented rice (e.g., content of Xuezhikang capsules, which is a dry powder), performing ultrasonic extraction once or more times with one or more organic solvents selected from the group consisting of dichloromethane, ethyl acetate, acetone, methanol, ethanol in 2-6 times by volume, 20-40 minutes each time, combining the extracted solutions, removing solvent to obtain a refined extract;

Optionally, the alcohol extract can be obtained by the following method: using 50%-100% ethanol or 50%-100% methanol in 2-6 times by volume as solvent to perform ultrasonic extraction once or more times, 20-40 minutes each time, combining extracted solutions, removing solvent to obtain the alcohol extract.

Without being restricted by any theory, because Xuezhikang itself is an alcohol extract of *Monascus*-fermented rice, *Monascus*-fermented rice can be directly used as raw material, and extracting steps are substantively the same for obtain the content of Xuezhikang, but *Monascus*-fermented rice has a relatively lower content of the compound. The specific strains of *Monascus*-fermented rice are not specifically limited, but include any strains of *Monascus*. Xuezhikang capsules (e.g., those manufactured by Beijing Peking University WBL Biotechnology Co., Ltd.) are commercially available in hospitals or pharmacies.

2) loading the refined extract obtained in step 1) on a silica gel column for separation, eluting in gradient manner with petroleum ether and ethyl acetate; the volume ratio of petroleum ether to ethyl acetate is 75:25, 50:50-25:75, 0:100 in sequence;

3) taking the elution fraction of petroleum ether-ethyl acetate (50:50-25:75) of step 2), subjecting to C18 reversed phase chromatography, using methanol-water for gradient elution, the volume ratio of methanol-water is 10:90, 50:50-75:25, 100:0 in sequence;

4) taking the elution fraction of methanol-water (50:50-75:25) of step 3), subjecting to purification with semi-preparative high performance liquid chromatography using acetonitrile-0.2% acetic acid aqueous solution (45:55) as mobile phase, C18 semi-preparative column as stationary phase, and collecting the fractions of chromatographic peak at 9.2 minute; and 5) freeze-drying the product of step 4) to obtain a compound of Formula I or Formula II.

The preparation method according to any one items of the present invention, meets any one or more of following items (1) to (9):

(1) in step 1), said organic solvent is preferably dichloromethane;

(2) in step 1), said ultrasonic extraction is performed for 3 times;

(3) in step 1), the solvent is removed by concentration under reduced pressure;

(4) in step 2), the volume ratio of petroleum ether-ethyl acetate is 75:25, 50:50, 25:75, 0:100 in sequence;

(5) in step 3), the elution fraction of petroleum ether-ethyl acetate (50:50 or 25:75) of step 2) is taken;

It is found by the inventors that all elution fractions of petroleum ether-ethyl acetate (50:50-25:75) contain the compound of the present invention.

(6) in step 3), the volume ratio of methanol-water is 10:90, 50:50, 75:25, 100:0 in sequence;

(7) in step 4), the elution fraction of methanol-water (50:50 or 75:25) of step 3) is taken;

It is found by the inventors that all elution fractions of methanol-water (50:50-75:25) contain the compound of the present invention.

(8) in step 4), the fractions of collected chromatographic peak at 9.2 minute are combined; and (9) in step 5), the conditions for freeze-drying are: cold trap temperature is −40° C. to −85° C., vacuum degree is 0-100 Pa; preferably, cold trap temperature is −50° C. to −82.7° C., vacuum degree is 2-13 Pa; more preferably, cold trap temperature is −82.7° C., vacuum degree is 2 Pa, or cold trap temperature is −50° C., vacuum degree is 8.5 Pa.

Further another aspect of the present invention relates to a method for preparing a compound of Formula II, comprising the following steps:

using hexahydroxyergosterol (e.g., 3,16,20,22,23,25-hexahydroxy-ergosterol, briefly called as Compound A) as substrate, dehydrating in the presence of p-toluenesulfonic acid monohydrate or 2,4,6-triisopropylsulfonyl chloride to generate a compound of Formula II:

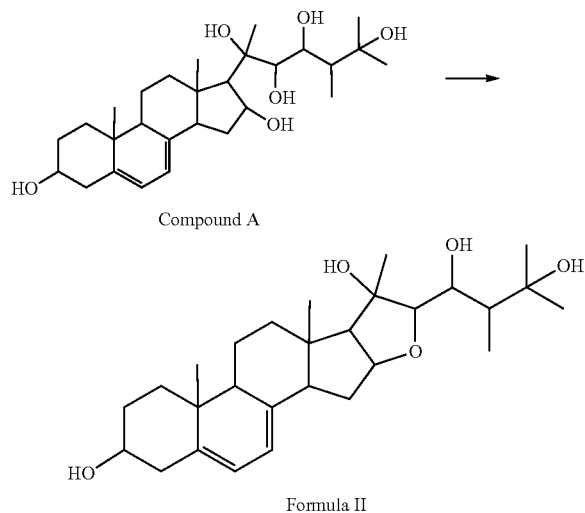

The Compound A can be prepared by referring to the preparation method of Chinese Patent Publication CN101469014A (application number is 200710304346.0).

In one embodiment of the present invention, the molar ratio of Compound A to p-toluenesulfonic acid monohydrate is 5:1-2:1; specifically, Compound A and p-toluenesulfonic acid monohydrate in toluene solution react under refluxing for 5-10 hours to obtain the compound of Formula II.

In one embodiment of the present invention, the molar ratio of Compound A to 2,4,6-triisopropylsulfonyl chloride is 5:1 to 2:1; specifically, Compound A and 2,4,6-triisopropylsulfonyl chloride in pyridine solution react at a temperature of 30° C. to 70° C. for 10 to 30 hours to obtain the compound of Formula II.

The compound of Formula II under certain conditions can generate different derivatives, such as ester derivatives, including but not being limited to acetate, sulfonate.

The ester derivatives can be prepared by reacting a compound of Formula II with a common anhydride, acyl chloride, sulfonyl chloride, sulfonic acid. A catalyst useful in reaction with anhydride can be selected from pyridine, concentrated sulfuric acid, $NaHCO_3$, etc. For examples:

Tetraacetate of compound of Formula II (corresponding to a compound of Formula I, in which $R_1=R_2=R_3=R_4=OC(=O)-CH_3$) is prepared by: reacting a compound of Formula II with acetic anhydride as reaction agent and solvent in the presence of a catalytic amount of concentrated sulfonic acid at 40-80° C. for 1-3 hours.

Tetra-p-tolylsulfonate of compound of Formula II (corresponding to a compound of Formula I, in which $R_1=R_2=R_3=R_4=$-OTs) is prepared by: reacting a compound of Formula II with p-toluenesulfonyl chloride in molar ratio of 1:4 to 1:8 in dichloromethane at 20-40° C. in the presence of triethylamine as acid scavenging agent.

Tetra(trifluoromethylsulfonate) of compound of Formula II (corresponding to a compound of Formula I, in which $R_1=R_2=R_3=R_4=CF_3SO_3-$) is prepared by: reacting a compound of Formula II with trifluoromethanesulfonic anhydride in molar ratio of 1:4 to 1:6 in dichloromethane at 20-30° C. in the presence of pyridine for 1-5 hours.

A compound of Formula II under certain conditions can also form silyl ether derivative, such as tert-butyl-dimethyl silyl ether of compound of Formula II. For example:

Tetra(tert-butyl-dimethyl silyl ether) of compound of Formula II (corresponding to a compound of Formula I, in which $R_1=R_2=R_3=R_4=$TBDMSO−) is prepared by: reacting a compound of Formula II with sodium hydride in molar ratio of 1:4 in tetrahydrofuran, then reacting with tert-butyl-dimethylchlorosilane at 20-40° C. for 1-3 hours.

Further another aspect of the present invention relates to an extract, which comprises a compound of Formula II of the present invention.

The extract according to any one of items of the present invention is an extract of dry powder of content of Xuezhikang capsules or an extract of *Monascus*-fermented rice.

In the extract according to any one of items of the present invention, the compound of Formula II has a content of 0.0001-5% (w/w), 0.001-2% (w/w) or 0.001-1% (w/w). The content of compound of Formula II can be regulated by appropriate concentration of the extract of the present invention. The concentration can be performed by a common method known by those skilled in the art.

The extract according to any one of items of the present invention is any one of following (1) to (3):

(1) the elution fraction of petroleum ether-ethyl acetate (50:50-25:75) as prepared in the above steps 1) to 2); preferably, the elution fraction of ((50:50 or 25:75); further preferably, the elution fraction of petroleum ether-ethyl acetate (25:75).

(2) the elution fraction of methanol-water (50:50-75:25) as prepared in the above steps 1) to 3); preferably, the elution fraction of methanol-water (75:25); and (3) the fractions of chromatographic peak at 9.2 minute as prepared in the above steps 1) to 4).

Further another aspect of the present invention relates to a composition, which comprises a compound of Formula I or Formula II, and/or the extract of any one of items of the present invention; optionally, further comprises a pharmaceutically acceptable carrier or excipient. Specifically, the composition is a pharmaceutical composition.

Usually, the pharmaceutical composition of the present invention comprises 0.1-90 wt % of a compound of Formula I or Formula II and/or pharmaceutically acceptable salt thereof. The pharmaceutical composition can be prepared according to a known method in the art. If necessary, the compound of Formula I or Formula II and/or pharmaceutically acceptable salt thereof can be combined with one or more solid or liquid pharmaceutically acceptable excipients and/or adjuvants to obtain a suitable administration form or dosage form.

The compound of Formula I or Formula II or pharmaceutically acceptable salt thereof or pharmaceutical composition comprising it of the present invention can be administrated in unit dosage form, and administration route can be intestinal administration or parenteral administration, such as oral, muscle, subcutaneous, nasal, mouth mucosa, skin, peritoneum, or rectum administration. Administration dosage form can be, for example, tablets, capsules, dripping pills, aerosols, pills, powders, solutions, suspensions, emulsions, granules, liposomes, transdermal agents, buccal tablets, suppositories, and lyophilized powder injections. They can be normal preparations, sustained-release preparations, controlled-release preparations and various particulate delivery systems. In order to prepare tablets as unit dosage form for administration, various carriers known in the art can be widely used. Examples of carrier are, for example, diluents and absorbents, such as starch, dextrin, calcium sulfate, lactose, mannitol, sucrose, sodium chloride, glucose, urea, calcium carbonate, kaolin, microcrystalline cellulose, aluminum silicate, etc.; wetting agents and binding agents, such as water, glycerol, polyethylene glycol, ethanol, propanol, starch slurry, dextrin, syrup, honey, glucose solution, acacia mucilage, gelatin mucilage, sodium carboxymethylcellulose, shellac, methylcellulose, potassium phosphate, polyvinylpyrrolidone; disintegrants, such as dry starch, alginates, agar powders, laminarin, sodium bicarbonate and citric acid, calcium carbonate, polyoxyethylene, sorbitol fatty acid esters, sodium dodecyl sulfate, methyl cellulose, ethyl cellulose; disintegration inhibitors, such as sucrose, tristearin, cocoa butter, hydrogenated oil; absorption enhancers, such as quaternary ammonium salts, sodium dodecyl sulfate; lubricants, such as talc powders, silicon dioxide, corn starch, stearates, boric acid, liquid paraffin, polyethylene glycol. They can also be further processed to form coated tablets, such as sugar coated tablets, thin membrane coated tablets, enteric-coated tablets, or double-layer tablets or multiple-layer tablets. In order to prepare pills as administration unit, various carriers known in the art can be widely used. The example of carriers are, for example, diluents or absorbents, such as glucose, lactose, starch, cocoa butter, hydrogenated vegetable oil, polyvinylpyrrolidone, Gelucire, kaolin, talc powder, etc.; binding agents, such as acacia gum, tragacanth gum, gelatin, ethanol, honey, liquid sugar, rice paste or flour paste, etc.; disintegrating agents, such as agar powder, dry starch, alginates, sodium dodecyl sulfate, methyl cellulose, ethyl cellulose, etc. In order to prepare suppositories as administration unit, various carriers known in the art can be widely used. The examples of carriers are, for example, polyethylene glycol, lecithin, cocoa butter, fatty alcohols, esters of fatty alcohols, gelatin, semi-synthesized glycerides, etc. In order to prepare capsules as administration unit, the compound of Formula I or Formula II or pharmaceutically acceptable salt thereof as effective ingredient is mixed with the above various carriers, and the obtained mixture is filled in hard gelatin capsules or soft capsules. The compound of Formula I or Formula II or pharmaceutically acceptable salt thereof as effective ingredient can also be processed to form microcapsules, then suspended in aqueous medium to form a suspension, or filled in hard capsules or processed to form an injection. In order to prepare injectable preparations as administration unit, for example, solutions, emulsions, lyophilized powder injections and suspensions, all diluents commonly used in the art can be used, for example, water, ethanol, polyethylene glycol, propane-1,3-diol, ethoxylated isostearyl alcohol, multiple-oxidized isostearyl alcohol, polyoxyethylene sorbitol fatty acid ester, etc. In addition, in order to prepare isotonic injection solutions, a suitable amount of sodium chloride, glucose or glycerol can be added to injection preparations, and conventional auxiliary solvents, buffers, pH regulators and so on can also be added.

In addition, if necessary, coloring agents, preservatives, perfumes, correctants, sweetening agents or other materials can also be added to the pharmaceutical preparations.

The dose of the compound of Formula I or Formula II or pharmaceutically acceptable salt thereof of the present invention depends on many factors, such as property and severity of the disease to be prevented or treated, patient's or animal's gender, age, bodyweight and individual reaction, the specific compound to be used, administration route, and administration frequency. The dose can be administered in single dose form or in several batches, such as 2-, 3- or 3-batches.

The term "composition" in the text refers to a product comprising various components in designated amounts, and any product directly or indirectly derived from various components in designated amounts in combination.

The actual dose levels of various active components in the pharmaceutical composition of the present invention can be changed so that the expected therapeutic effects can be achieved via the resultant amount relative to specific patient, composition and administration manner. The dose level must be selected according to the activity of the specific compound, administration route, severity of disease to be treated, patient's condition and medical history. However, the practice in the art is that the dose of compound gradually increases from a level lower than that for achieving the desired therapeutical effects to a dose capable of achieving the desired therapeutical effects.

Further another aspect of the present invention relates to use of the compound of the present invention or the extract of any one of items of the present invention or the composition of the present invention in the manufacture of a medicament for reduction or regulation of blood-fat or prophylaxis and/or treatment of dyslipidemia, hyperlipemia, hypercholesterolemia, or atherosclerotic.

Further another aspect of the present invention relates to use of the compound of the present invention or the extract of any one of items of the present invention or the composition of the present invention in the manufacture of a HMG-CoA reductase inhibitor.

Further another aspect of the present invention relates to a method for inhibiting HMG-CoA reductase in vivo or in vitro, comprising the step of using an effective amount of the compound of the present invention or the extract of any one of items of the present invention or the composition of the present invention.

The experimental results of Example 1 confirm that the compound of the present invention has activity of inhibiting HMG-CoA reductase, and the activity is dose dependent.

Further another aspect of the present invention relates to a method for reduction or regulation of blood-fat or prophylaxis and/or treatment and/or adjunctive treatment of dyslipidemia, hyperlipemia, hypercholesterolemia, or atherosclerotic, comprising the step of administering an effective amount of the compound of the present invention or the extract of any one of items of the present invention or the composition of the present invention.

Further another aspect of the present invention relates to use of the compound of the present invention or the extract of any one of items of the present invention or the composition of the present invention in the manufacture of a medicament for prophylaxis and/or treatment and/or adjunctive treatment of a cancer; specifically, said cancer is colon cancer, liver cancer, lymph cancer, or melanoma.

Further another aspect of the present invention relates to use of the compound of the present invention or the extract of any one of items of the present invention or the composition of the present invention in the manufacture of a medicament or an agent for inhibiting tumor cells; specifically, said tumor cells are colon cancer cells, liver cancer cells, lymph cancer cells, or melanoma cells.

Further another aspect of the present invention relates to a method for inhibiting tumor cells, comprising the step of using an effective amount of the compound of the present invention or the extract of any one of items of the present invention or the composition of the present invention; specifically, said tumor cells are colon cancer cells, liver cancer cells, lymph cancer cells, or melanoma cells. Specifically, the method for inhibiting tumor cells is a method for inhibiting tumor cells in vitro or in vivo.

The experimental results of Example 2 confirm the compound of the present invention can effectively inhibit tumor cells.

Further another aspect of the present invention relates to a method for prophylaxis and/or treatment and/or adjunctive treatment of a cancer, comprising the step of using an effective amount of the compound of the present invention or the extract of any one of items of the present invention or the composition of the present invention; specifically, said cancer is colon cancer, liver cancer, lymph cancer, or melanoma.

Further another aspect of the present invention relates to use of the compound of the present invention or the extract of any one of items of the present invention or the composition of the present invention in the manufacture of a medicament or for prophylaxis and/or treatment and/or adjunctive treatment of obesity or a disease associated with obesity anti-obesity agent; specifically, said disease associated with obesity is hyperlipidemia, atherosclerosis, coronary heart disease, or diabetes.

Further another aspect of the present invention relates to use of the compound of the present invention or the extract of any one of items of the present invention or the composition of the present invention in the manufacture of a medicament or an agent for inhibiting lipase.

Further another aspect of the present invention relates to a method for inhibiting lipase, comprising the step of using an effective amount of the compound of the present invention or the extract of any one of items of the present invention or the composition of the present invention. Specifically, said method for inhibiting lipase is a method for inhibiting lipase in vivo or in vitro.

The experimental results of Example 3 confirm the compound of the present invention can effectively inhibit lipase.

Further another aspect of the present invention relates to a method for prophylaxis and/or treatment and/or adjunctive treatment of obesity or a disease associated with obesity or a method for losing weight; specifically, said disease associated with obesity is hyperlipidemia, atherosclerosis, coronary heart disease, or diabetes.

In the aforementioned treatment and/or prophylaxis and/or adjunctive treatment, a compound of the present invention in a therapeutically and/or prophylactically and/or adjunctively therapeutically effective amount can be used in form of pure compound, or in form of pharmaceutically acceptable esters or predrugs thereof (if they exist). Alternatively, the compound can be administered via a pharmaceutical composition comprising the compound and one or more pharmaceutically acceptable excipients. It should be understood that the total amount per day of the compound or composition of the present invention must be determined by a physician within the range of reliable medical decisions. As for any specific patients, the specific therapeutically amount must be determined based on various factors, including the diseases to be treated and severity thereof, the activity of the used specific compound, the used specific composition, the age, body weight, general health status, gender and food of patient, the administration time and route and excretory rate of the used specific compound, the drug(s) administered in combination or simultaneously with the specific compound, and similar factors well known in the art of medicine. For example, it is a common method in the art to increase gradually the dose of compound from a level lower than that for achieving desired therapeutical effects to a level enough to achieve the desired therapeutical effects. In general, the dose of a compound of Formula I for mammals especially human can be 0.001-1000 mg/kg body weight per day, such as 0.01-100 mg/kg body weight per day, 0.01-10 mg/kg body weight per day.

The compound according to the present invention can effectively prevent and/or treat the various diseases and disorders as mentioned in the present invention.

In the present invention, the term "$C_1$-$C_3$ alkyl" comprises methyl, ethyl, propyl and isopropyl.

The term "obesity" includes but is not limited to simple obesity (without a significant cause in internal secretion and metabolism, relating to heredity and feeding habits), secondary obesity (usually associating to some diseases such as hyperadrenocorticism, which could be eliminated when the diseases are cured). The obesity can be obesity in a mammal, and the mammal comprises human and pig.

The term "disease associated with obesity" includes but is not limited to hyperlipidemia, atherosclerosis, coronary heart disease, or diabetes.

The term lipase (enzyme classification number: EC3.1.1.3) includes but is not limited to a lipase of mammal, such as a lipase of human or a lipase of pig, the lipase of human can be human pancreatic lipase, and the lipase of pig can be porcine pancreatic lipase.

The term "effective amount" refers to a dose that can fulfill treatment, prophylaxis and or remission of the diseases or disorders of the present invention in a subject.

In the present invention, if not specifically described, a percentage content of an ingredient refers to a weight percentage (w/w).

The present invention further relates to the following aspects 1 to 22:

1. Use of any one of items (1) to (4) in the manufacture of a medicament for prophylaxis and/or treatment and/or adjunctive treatment of a cancer; specifically, said cancer is colon cancer, liver cancer, lymph cancer, or melanoma, (1) a compound of Formula I or a pharmaceutically acceptable salt thereof, Formula I

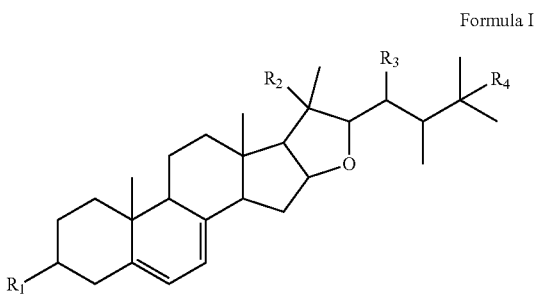

wherein, $R_1$ is selected from the group consisting of —OH, =O, H, and $C_1$-$C_3$ alkyl;

$R_2$ is selected from the group consisting of —OH, H, and $C_1$-$C_3$ alkyl;

$R_3$ is selected from the group consisting of —OH, =O, H, and $C_1$-$C_3$ alkyl;

$R_4$ is selected from the group consisting of —OH, H, and $C_1$-$C_3$ alkyl;

and 2, 3 or 4 of any of $R_1$, $R_2$, $R_3$, and $R_4$ are simultaneously —OH;

(2) a compound of Formula II or a pharmaceutically acceptable salt thereof,

Formula II

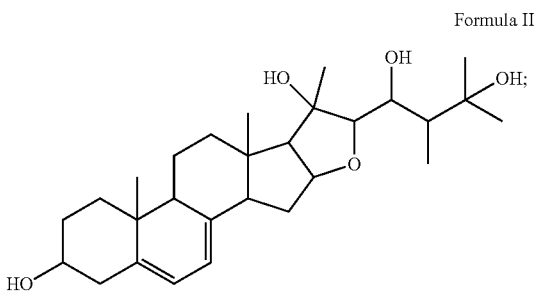 [SMILES: CC(C(O)C1OC2CC3C4=CC=C5CC(O)CCC5(C)C4CCC3(C)C2C1(C)O)C(C)(C)O]

(3) an extract, which comprises a compound of Formula II; and (4) a composition, which comprises any one of the above items (1)-(3).

2. Use of any one of items (1) to (4) of Aspect 1 in the manufacture of a medicament or an agent for inhibiting tumor cells in vivo or in vitro; specifically, said tumor cells are colon cancer cells, liver cancer cells, lymph cancer cells, or melanoma cells.

3. The use according to Aspect 1 or 2, wherein the extract of item (3) is an extract of *Monascus*-fermented rice and/or an extract of an alcohol extract of *Monascus*-fermented rice (e.g., content of Xuezhikang capsules).

4. The use according to Aspect 3, wherein the extract of item (3) is an elution fraction of petroleum ether-ethyl acetate (50:50-25:75) as prepared in the following steps 1) to 2); or an elution fraction of methanol-water (50:50-75:25) as prepared in the following steps 1) to 3); or fractions of chromatographic peak at 9.2 minute as prepared in the following steps 1) to 4):

1) providing *Monascus*-fermented rice and/or alcohol extract of *Monascus*-fermented rice (e.g., content of Xuezhikang capsules, which is a dry powder), performing ultrasonic extraction once or more times with one or more organic solvents selected from the group consisting of dichloromethane, ethyl acetate, acetone, methanol, ethanol in 2-6 times by volume, 20-40 minutes each time, combining the extracted solutions, removing solvent to obtain a refined extract;

2) subjecting the refined extract obtained in step 1) to chromatography separation with a silica gel column, eluting in gradient manner with petroleum ether and ethyl acetate; the volume ratio of petroleum ether to ethyl acetate is 75:25, 50:50-25:75, 0:100 in sequence;

3) taking the elution fraction of petroleum ether-ethyl acetate (50:50-25:75) of step 2), subjecting to chromatography separation with a C18 reversed column, using methanol-water for gradient elution, the volume ratio of methanol-water is 10:90, 50:50-75:25, 100:0 in sequence; and 4) taking the elution fraction of methanol-water (50:50-75:25) of step 3), subjecting to purification with semi-preparative high performance liquid chromatography using acetonitrile-0.2% acetic acid aqueous solution (45:55) as mobile phase, C18 semi-preparative column as stationary phase, and collecting fractions of chromatographic peak at 9.2 minute.

5. The use according to Aspect 4, characterized in any one or more of items (1) to (8):

(1) in step 1), said organic solvent is dichloromethane;

(2) in step 1), said ultrasonic extraction is performed for 3 times;

(3) in step 1), the solvent is removed by concentration under reduced pressure;

(4) in step 2), the volume ratio of petroleum ether-ethyl acetate is 75:25, 50:50, 25:75, 0:100 in sequence;

(5) in step 3), the elution fraction of petroleum ether-ethyl acetate (50:50 or 25:75) of step 2) is taken;

(6) in step 3), the volume ratio of methanol-water is 10:90, 50:50, 75:25, 100:0 in sequence;

(7) in step 4), the elution fraction of methanol-water (50:50 or 75:25) of step 3) is taken;

(8) in step 4), the fractions of collected chromatographic peak at 9.2 minute are combined.

6. The use according to Aspect 1 or 2, wherein the composition of item (4) further comprises a pharmaceutically acceptable carrier or excipient.

7. A method for inhibiting tumor cells in vivo or in vitro, comprising the step of using an effective amount of any one of the items (1) to (4) of Aspect 1; specifically, said tumor cells are colon cancer cells, liver cancer cells, lymph cancer cells, or melanoma cells.

8. The method according to Aspect 7, wherein the extract of item (3) is an extract of *Monascus*-fermented rice and/or an extract of an alcohol extract of *Monascus*-fermented rice (e.g., content of Xuezhikang capsules).

9. The method according to claim 8, wherein the extract of item (3) is the elution fraction of petroleum ether-ethyl acetate (50:50-25:75) as prepared in the following steps 1) to 2); or the elution fraction of methanol-water (50:50-75:25) as prepared in the following steps 1) to 3); or fractions of chromatographic peak at 9.2 minute as prepared in the following steps 1) to 4):

1) providing *Monascus*-fermented rice and/or alcohol extract of *Monascus*-fermented rice (e.g., content of Xuezhikang capsules, which is a dry powder), performing ultrasonic extraction once or more times with one or more organic solvents selected from the group consisting of dichloromethane, ethyl acetate, acetone, methanol, ethanol in 2-6 times by volume, 20-40 minutes each time, combining the extracted solutions, removing solvent to obtain a refined extract;

2) subjecting the refined extract obtained in step 1) to chromatography separation with a silica gel column, eluting in gradient manner with petroleum ether and ethyl acetate; the volume ratio of petroleum ether to ethyl acetate is 75:25, 50:50-25:75, 0:100 in sequence;

3) taking the elution fraction of petroleum ether-ethyl acetate (50:50-25:75) of step 2), subjecting to chromatography separation with a C18 reversed column, using methanol-water for gradient elution, the volume ratio of methanol-water is 10:90, 50:50-75:25, 100:0 in sequence; and 4) taking the elution fraction of methanol-water (50:50-75:25) of step 3), subjecting to purification with semi-preparative high performance liquid chromatography using acetonitrile-0.2% acetic acid aqueous solution (45:55) as mobile phase, C18 semi-preparative column as stationary phase, and collecting fractions of chromatographic peak at 9.2 minute.

10. The method according to Aspect 9, characterized in any one or more of items (1) to (8):

(1) in step 1), said organic solvent is dichloromethane;

(2) in step 1), said ultrasonic extraction is performed for 3 times;

(3) in step 1), the solvent is removed by concentration under reduced pressure;

(4) in step 2), the volume ratio of petroleum ether-ethyl acetate is 75:25, 50:50, 25:75, 0:100 in sequence;

(5) in step 3), the elution fraction of petroleum ether-ethyl acetate (50:50 or 25:75) of step 2) is taken;

(6) in step 3), the volume ratio of methanol-water is 10:90, 50:50, 75:25, 100:0 in sequence;

(7) in step 4), the elution fraction of methanol-water (50:50 or 75:25) of step 3) is taken;

(8) in step 4), the fractions of collected chromatographic peak at 9.2 minute are combined.

11. The method of Aspect 7, wherein the composition of item (4) further comprises a pharmaceutically acceptable carrier or excipient.

12. Use of any one of items (1) to (4) in the manufacture of a medicament for prophylaxis and/or treatment and/or adjunctive treatment of obesity or a disease associated with obesity or an anti-obesity agent; specifically, said disease associated with obesity is hyperlipidemia, atherosclerosis, coronary heart disease, or diabetes.

(1) a compound of Formula I or a pharmaceutically acceptable salt thereof,

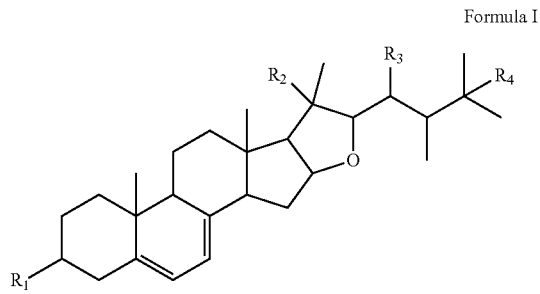

Formula I wherein, $R_1$ is selected from the group consisting of —OH, =O, H, and $C_1$-$C_3$ alkyl;

$R_2$ is selected from the group consisting of —OH, H, and $C_1$-$C_3$ alkyl;

$R_3$ is selected from the group consisting of —OH, =O, H, and $C_1$-$C_3$ alkyl;

$R_4$ is selected from the group consisting of —OH, H, and $C_1$-$C_3$ alkyl;

and 2, 3 or 4 of any of $R_1$, $R_2$, $R_3$, and $R_4$ are simultaneously —OH;

(2) a compound of Formula II or a pharmaceutically acceptable salt thereof,

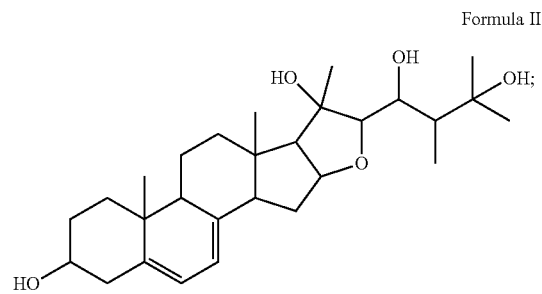 [SMILES: CC(C(O)C1OC2CC3C4=CC=C5CC(O)CCC5(C)C4CCC3(C)C2C1(C)O)C(C)(C)O]

Formula II (3) an extract, which comprises a compound of Formula II; and (4) a composition, which comprises any one of the above items (1)-(3).

13. Use of any one of items (1) to (4) of Aspect 12 in the manufacture of a medicament or an agent for inhibiting lipase in vivo or in vitro.

14. The use according to Aspect 12 or 13, wherein the extract of item (3) is an extract of *Monascus*-fermented rice and/or an extract of an alcohol extract of *Monascus*-fermented rice (e.g., content of Xuezhikang capsules).

15. The use according to Aspect 14, wherein the extract of item (3) is the elution fraction of petroleum ether-ethyl acetate (50:50-25:75) as prepared in the following steps 1) to 2); or the elution fraction of methanol-water (50:50-75:25) as prepared in the following steps 1) to 3); or fractions of chromatographic peak at 9.2 minute as prepared in the following steps 1) to 4):

1) providing *Monascus*-fermented rice and/or alcohol extract of *Monascus*-fermented rice (e.g., content of Xuezhikang capsules, which is a dry powder), performing ultrasonic extraction once or more times with one or more organic solvents selected from the group consisting of dichloromethane, ethyl acetate, acetone, methanol, ethanol in 2-6 times by volume, 20-40 minutes each time, combining the extracted solutions, removing solvent to obtain a refined extract;

2) subjecting the refined extract obtained in step 1) to chromatography separation with a silica gel column, eluting in gradient manner with petroleum ether and ethyl acetate; the volume ratio of petroleum ether to ethyl acetate is 75:25, 50:50-25:75, 0:100 in sequence;

3) taking the elution fraction of petroleum ether-ethyl acetate (50:50-25:75) of step 2), subjecting to chromatography separation with a C18 reversed column, using methanol-water for gradient elution, the volume ratio of methanol-water is 10:90, 50:50-75:25, 100:0 in sequence; and 4) taking the elution fraction of methanol-water (50:50-75:25) of step 3), subjecting to purification with semi-preparative high performance liquid chromatography using acetonitrile-0.2% acetic acid aqueous solution (45:55) as mobile phase, C18 semi-preparative column as stationary phase, and collecting fractions of chromatographic peak at 9.2 minute.

16. The use according to Aspect 15, characterized in any one or more of items (1) to (8):

(1) in step 1), said organic solvent is dichloromethane;

(2) in step 1), said ultrasonic extraction is performed for 3 times;

(3) in step 1), the solvent is removed by concentration under reduced pressure;

(4) in step 2), the volume ratio of petroleum ether-ethyl acetate is 75:25, 50:50, 25:75, 0:100 in sequence;

(5) in step 3), the elution fraction of petroleum ether-ethyl acetate (50:50 or 25:75) of step 2) is taken;

(6) in step 3), the volume ratio of methanol-water is 10:90, 50:50, 75:25, 100:0 in sequence;

(7) in step 4), the elution fraction of methanol-water (50:50 or 75:25) of step 3) is taken;

(8) in step 4), the fractions of collected chromatographic peak at 9.2 minute are combined.

17. The use according to Aspect 12 or 13, wherein the composition of item (4) further comprises a pharmaceutically acceptable carrier or excipient.

18. A method for inhibiting lipase in vivo or in vitro, comprising a step of using an effective amount of any one of the items (1) to (4) of Aspect 12.

19. The method according to Aspect 18, wherein the extract of item (3) is an extract of *Monascus*-fermented rice and/or an extract of an alcohol extract of *Monascus*-fermented rice (e.g., content of Xuezhikang capsules).

20. The method according to claim 19, wherein the extract of item (3) is the elution fraction of petroleum ether-ethyl acetate (50:50-25:75) as prepared in the following steps 1) to 2); or the elution fraction of methanol-water (50:50-75:25) as prepared in the following steps 1) to 3); or fractions of chromatographic peak at 9.2 minute as prepared in the following steps 1) to 4):

1) providing *Monascus*-fermented rice and/or alcohol extract of *Monascus*-fermented rice (e.g., content of Xuezhikang capsules, which is a dry powder), performing ultrasonic extraction once or more times with one or more organic solvents selected from the group consisting of dichloromethane, ethyl acetate, acetone, methanol, ethanol in 2-6 times by volume, 20-40 minutes each time, combining the extracted solutions, removing solvent to obtain a refined extract;

2) subjecting the refined extract obtained in step 1) to chromatography separation with a silica gel column, eluting in gradient manner with petroleum ether and ethyl acetate; the volume ratio of petroleum ether to ethyl acetate is 75:25, 50:50-25:75, 0:100 in sequence;

3) taking then elution fraction of petroleum ether-ethyl acetate (50:50-25:75) of step 2), subjecting to chromatography separation with a C18 reversed column, using methanol-water for gradient elution, the volume ratio of methanol-water is 10:90, 50:50-75:25, 100:0 in sequence; and 4) taking the elution fraction of methanol-water (50:50-75:25) of step 3), subjecting to purification with semi-preparative high performance liquid chromatography using acetonitrile-0.2% acetic acid aqueous solution (45:55) as mobile phase, C18 semi-preparative column as stationary phase, and collecting fractions of chromatographic peak at 9.2 minute.

21. The method according to Aspect 20, characterized in any one or more of items (1) to (8):

(1) in step 1), said organic solvent is dichloromethane;

(2) in step 1), said ultrasonic extraction is performed for 3 times;

(3) in step 1), the solvent is removed by concentration under reduced pressure;

(4) in step 2), the volume ratio of petroleum ether-ethyl acetate is 75:25, 50:50, 25:75, 0:100 in sequence;

(5) in step 3), the elution fraction of petroleum ether-ethyl acetate (50:50 or 25:75) of step 2) is taken;

(6) in step 3), the volume ratio of methanol-water is 10:90, 50:50, 75:25, 100:0 in sequence;

(7) in step 4), the elution fraction of methanol-water (50:50 or 75:25) of step 3) is taken;

(8) in step 4), the fractions of collected chromatographic peak at 9.2 minute are combined.

22. The method of Aspect 18, wherein the composition of item (4) further comprises a pharmaceutically acceptable carrier or excipient.

BENEFICIAL EFFECTS OF THE INVENTION

1. The compound of the present invention can effectively inhibit HMG-CoA reductase, and has dose-dependent activity for inhibiting HMG-CoA reductase; so that it is a potential drug for reduction or regulation of blood-fat or for prophylaxis and/or treatment of dyslipidemia, hyperlipemia, hypercholesterolemia, or atherosclerotic.

2. The compound of the present invention can effectively inhibit the proliferation of cancer cells (tumor cells), and has inhibition activity in concentration-effect relation; so that it is a potential drug for prophylaxis and/or treatment and/or adjunctive treatment of cancers.

3. The compound of the present invention can effectively inhibit the activity of lipase, and has inhibition activity in concentration-effect relation; so that it is a potential drug for prophylaxis and/or treatment and/or adjunctive treatment of obesity or diseases associated with obesity.

SPECIFIC MODELS FOR CARRYING OUT THE INVENTION

Figure 1:
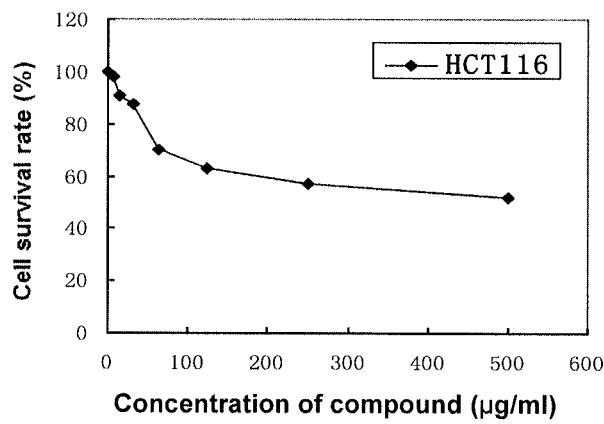
FIG. 1: inhibition curve of a compound of Formula II on growth of HCT116 cells.

The present invention is further illustrated with the following examples, but those skilled in the art would understand the following examples are merely used to illustrate the present invention, rather than to limit the protection scope of the present invention. For those technologies or conditions not specifically described in the examples, they were performed according to the technologies or conditions as described in the documents in the art or according to the product specifications. For those reagents and instruments whose manufacturers were not given, they were all conventional products commercially available in markets.

Example 1: Preparation of Compound of Formula II (1)

Operation Steps:

1) About 1 kg of dry powder of content of Xuezhikang capsules (produced by Beijing Peking University WBL Biotechnology Co., Ltd.) was provided, ultrasonic extraction was performed for 3 times with dichloromethane in 2-6 times by volume as solvent, 20-40 minutes for each time, all extracted solutions were combined, concentrated and subjected to solvent recovery under reduced pressure, to obtain 91 g of dichloromethane refined extract.

2) 50 g of the dichloromethane refined extract was loaded on silica gel column for chromatography separation, and eluted in gradient manner with petroleum ether and ethyl acetate. The volume ratio of petroleum ether-ethyl acetate was 75:25, 50:50, 25:75, 0:100 in sequence.

3) 5.0 g of fraction of petroleum ether-ethyl acetate (25:75) was taken, separated with C18 reversed column chromatography, eluted with methanol-water (10:90-100:0) in gradient manner to obtain 4 fractions (methanol-water 10:90, 50:50, 75:25, 100:0), in which 1.3 g of the elution fraction of methanol-water (75:25) was purified with semi-preparative high performance liquid chromatography, acetonitrile-0.2% acetic acid aqueous solution (45:55) was used as mobile phase, flow rate was 4 mL/min, C18 semi-preparative chromatography column (10×250 mm, 5 μm) was stationary phase, detection wavelength of DAD detector was 270 nm, chromatographic peaks at 9.2 minute were collected, accumulated for many times, then concentrated, freeze-dried to obtain about 40 mg of the compound.

Example 2: Preparation of Compound of Formula II (2)

Operation Steps:

1) 5 kg of dry powder of *Monascus*-fermented rice was provided, ultrasonic extraction was performed for 3 times with dichloromethane in 2-6 times by volume as solvent, 20-40 minutes for each time, all extracted solutions were combined, concentrated and subjected to solvent recovery under reduced pressure, to obtain 78 g of dichloromethane refined extract.

2) 30 g of the dichloromethane refined extract was loaded on silica gel column for chromatography separation, and eluted in gradient manner with petroleum ether and ethyl acetate. The volume ratio of petroleum ether-ethyl acetate was 75:25, 50:50, 25:75, 0:100 in subsequence.

3) 3.0 g of fraction of petroleum ether-ethyl acetate (25:75) was taken, separated with C18 reversed column chromatography, eluted with methanol-water (10:90-100:0) in gradient manner to obtain 4 fractions (methanol-water 10:90, 50:50, 75:25, 100:0), in which 0.8 g of the elution fraction of methanol-water (75:25) was purified with semi-preparative high performance liquid chromatography, acetonitrile-0.2% acetic acid aqueous solution (45:55) was used as mobile phase, flow rate was 4 mL/min, C18 semi-preparative chromatography column (10×250 mm, 5 μm) was stationary phase, detection wavelength of DAD detector was 270 nm, chromatographic peaks at 9.2 minute were collected, accumulated for many times, then concentrated, freeze-dried to obtain about 25 mg of the compound.

Example 3: Preparation of Compound of Formula II (3)

In a reaction flask, toluene (350 mL) was added, then Compound A (4.4 g, 9.2 mmol) and p-toluenesulfonic acid monohydrate (0.59 g, 3.1 mmol) were added, heated to refluxing and water was removed by azeotropism for 7 hours, cooled to room temperature after reaction, solvent was removed under reduced pressure, then silica gel column chromatograph was performed for purification, to obtain a sticky oily compound, i.e., compound of Formula II.

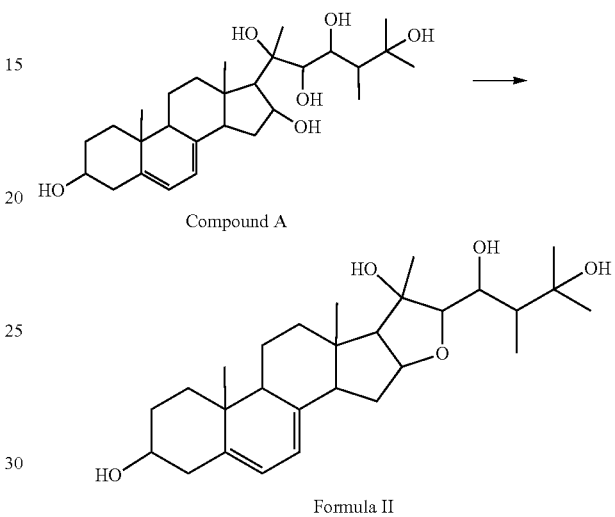

Compound A

Formula II

Example 4: Preparation of Compound of Formula II (4)

In a reaction flask, pyridine (100 mL) was added, then Compound A (4.4 g, 9.2 mmol) and 2,4,6-triisopropylsulfonyl chloride (0.93 g, 3.1 mmol) were added, heated and reacted at 50° C. for 20 hours, solvent was removed under reduced pressure, then silica gel column chromatograph was performed for purification, to obtain a sticky oily compound, i.e., compound of Formula II.

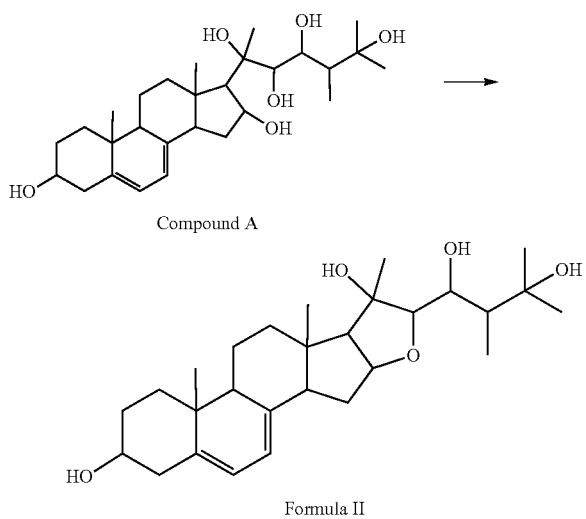

Compound A

Formula II

Example 5: Identification of Structure of Compounds

The samples used were compounds prepared in Examples 1, 2, 3, 4. The results confirmed that all compounds prepared in Examples 1-4 were the same, i.e., compound of Formula II.

1. Physical and Chemical Data of Compounds

White powder, optical rotation: $[\alpha]^{25}{}_D$-50.00 (c 0.118, CH$_2$Cl$_2$:MeOH=1:1);

UV spectrum showed 3 maximum absorption peaks, separately, $\Delta_{max}$(CH$_2$Cl$_2$:MeOH)=271.6 nm, 282.2 nm, 293.8 nm.

FT-IR (KBr, cm$^{-1}$) spectrum: 3392(—OH), 2969, 2933 (saturated hydrocarbon), 1652, 1647(C=C), 1456, 1378 (gem-dimethyl).

2. Determination of Molecular Formula

HR-ESI-MS gave m/z 483.3104 [M+Na]$^+$ (calcd. 483.3081, err 2.3), so that the molecular weight of the compound was deduced as 460.32. $^1$H-NMR and $^{13}$C-NMR showed that there were 40 hydrogen signals and 28 carbon signals. DEPT showed there were 6 quaternary carbons, 10 CH, 6 CH$_2$ and 6 CH$_3$. In $^{13}$C-NMR, 4 olefinic carbon signals were at 117.2 ppm, 119.6 ppm, 139.1 ppm and 140.6 ppm. The analysis of combining HSQC and $^{13}$C-NMR showed there were 6 oxygenated carbons linked to oxygen atoms at 70.5 ppm, 72.4 ppm, 74.5 ppm, 80.4 ppm, 83.8 ppm and 84.4 ppm. In view of molecular weight with $^1$H, $^{13}$C-NMR and DEPT spectra in combination, if the compound had 6 oxygen atoms, its molecular weight would exceed 460.32, thus it could be deduced that the compound should have 5 oxygen atoms and 4 hydrogen atoms that did not present signals in $^1$H-NMR spectrum. Thus, among the above 5 oxygen atoms, 4 oxygen atoms belonged to 4 hydroxyls, while the 5$^{th}$ oxygen existed in form of ether. According to the above analysis, it could be determined that the molecule had 28 carbon atoms, 44 hydrogen atoms, and 5 oxygen atoms, and the molecular formula was C$_{28}$H$_{44}$O$_5$.

3. Determination of the Chemical Structure

By analyzing the $^{13}$C-NMR and DEPT spectra of the compound, there were 28 carbon atoms, in which 6 carbon atoms were of methyl forms. Since 3 maximum absorption peaks at 271.6 nm, 282.2 nm and 293.8 nm in UV spectrum were substantively identical to those of ergosterol, it was primarily determined that the compound had framework of ergosterol. Its unsaturation degree was 7 based on calculation of molecular formula. Thus, it could be deduced that, besides 6 degrees of unsaturation including 2 double bonds and 4 rings of ergosterol framework, the compound further had one degree of unsaturation and it must be a ring, so that this ring could be determined as an epoxy formed with the 5$^{th}$ oxygen atom as center. The HSQC and HMBC spectra were analyzed in combination and showed that the 6 carbon atoms linked to oxygen atoms were separately assigned to 4 carbon atoms linked to 4 hydroxyls (70.5, 72.4, 74.5, 80.4 ppm) and 2 carbon atoms linked to the residual one oxygen atom (83.8, 84.4 ppm). Deep analysis of HMBC spectra showed that the 5$^{th}$ ring system was a 5-membered ring consisting of C-16 (83.8 ppm), C-17 (66.9 ppm), C-20 (80.4 ppm), C-22 (84.4 ppm) and oxygen atom. This satisfied degree of unsaturation and number of carbon atoms linked to oxygen atoms. Further analysis of mass spectrum gave molecular weight and molecular formula, which confirmed the above analysis. In sum, the above analysis indicated that the new compound was: 16,22-epoxy-ergosta-5,7-dien-3,20,23,25-tetraol. The chemical structure was shown in the following Formula II:

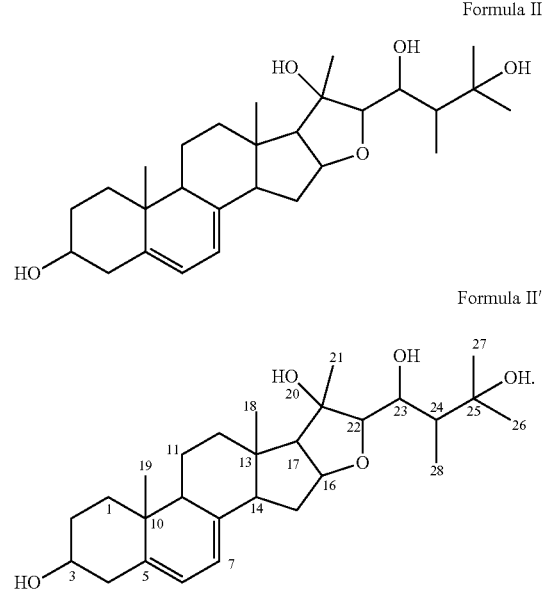

Formula II

Formula II'

4. NMR Data of Compound of Formula II
The data were shown in Table 1.

TABLE 1

NMR data of compound of Formula II
(600 MHz, CDCl$_3$, J in Hz)

| No. | $^1$H-NMR, (ppm) | $^{13}$C-NMR, (ppm) | DEPT | HMBC (H→C) |
|---|---|---|---|---|
| 1 | 1.28 (1H, m) <br> 1.90 (1H, m) | 38.4 | CH$_2$ | — |
| 2 | 1.48 (1H, m) <br> 1.89 (1H, m) | 32.1 | CH$_2$ | — |
| 3 | 3.62 (1H, m) | 70.5 | CH | — |
| 4 | 2.39 (1H, m) <br> 2.46 (1H, m) | 40.9 | CH$_2$ | — |
| 5 | — | 140.6 | C | — |
| 6 | 5.56 (1H, m) | 119.6 | CH | 4, 7 |
| 7 | 5.38 (1H, m) | 117.2 | CH | — |
| 8 | — | 139.1 | C | — |
| 9 | 1.95 (1H, m) | 46.0 | CH | — |
| 10 | — | 37.3 | C | — |
| 11 | 1.60 (1H, m) <br> 1.77 (1H, m) | 20.8 | CH$_2$ | — |
| 12 | 1.25 (1H, m) <br> 2.08 (1H, m) | 39.3 | CH$_2$ | — |
| 13 | — | 43.0 | C | — |
| 14 | 1.87 (1H, m) | 54.0 | CH | 13 |
| 15 | 1.75 (1H, m) <br> 2.23 (1H, m) | 34.2 | CH$_2$ | 14 |
| 16 | 4.66 (1H, m) | 83.8 | CH | 13, 14, 15 |
| 17 | 1.90 (1H, m) | 66.9 | CH | 20, 22 |
| 18 | 1.12 (3H, s) | 14.6 | CH$_3$ | 27, 12, 13, 14 |
| 19 | 0.96 (3H, s) | 16.6 | CH$_3$ | 9, 10, 1 |
| 20 | — | 80.4 | C | — |
| 21 | 1.43 (3H, s) | 27.8 | CH$_3$ | 20, 22, 24 |
| 22 | 4.19 (1H, brs) | 84.4 | CH | 21, 24, 23, 20 |
| 23 | 3.66 (1H, brd, J = 9.0 Hz) | 72.4 | CH | 28, 24, 25, 20 |
| 24 | 1.75 (1H, m) | 46.4 | CH | 27, 28 |
| 25 | — | 74.5 | | |
| 26 | 1.20 (3H, s) | 30.3 | CH$_3$ | 25, 24 |
| 27 | 1.23 (3H, s) | 24.0 | CH$_3$ | 25, 24 |
| 28 | 0.82 (3H, d, J = 7.2 Hz) | 14.0 | CH$_3$ | 23, 25, 24 |

Notation:
"—" represents concern signal does not exist.

Example 6: Preparation of Tetraacetate of Compound of Formula II

The mixture of Compound A (4.23 g, 9.2 mmol) and 2 drops of concentrated sulfuric acid in 20 mL of acetic anhydride was heated with water-bath to 50° C., reacted for 2 hours, cooled, added with saturated $NaHCO_3$ aqueous solution, extracted with toluene for 3 times, the organic layer was evaporated under rotation to obtain a product, and further purified by silica gel column chromatography to obtain tetraacetate of compound of Formula II via silica gel column chromatography. Pyridine catalysis could be used for prevention of configuration reversion.

Example 7: Preparation of Tetra-p-Tolylsulfonate of Compound of Formula II

In a dry 25 mL flask, compound of Formula II (4.23 g, 9.2 mmol) and 50 mL of dry dichloromethane were added, cooled to 0° C., p-tolylsulfonyl chloride (10.56 g, 55.3 mmol) was added, triethylamine (7.46 g, 73.6 mmol) was added dropwise under stirring. After end of dropwise adding, the reaction mixture solution was stirred at 20° C. for 1 hour, washed with water (50 mL×3), dried with anhydrous sodium sulfate, filtrated, dried out solvent by evaporation to obtain a crude product, and subjected to rapid column chromatography to obtain tetra-p-tolylsulfonate of compound of Formula II.

Example 8: Preparation of Tetra(Trifluoromethylsulfonate) of Compound of Formula II Compound of Formula II (4.23 g, 9.2 mmol) and pyridine (4.36 g, 55.2 mmol) were added in sequence into a flask containing 50 mL of dry dichloromethane under stirring, then trifluoromethylsulfonate (12.46 g, 44.2 mmol) was slowly added dropwise at room temperature (25° C.) within about 20 minutes, reacted for 2 hours, concentrated filtrate, the residue was subjected to separation with silica gel column chromatography to obtain tetra(trifluoromethylsulfonate) of compound of Formula II.

Example 9: Preparation of Tetra(Tert-Butyl-Dimethyl-Silyl Ether) of Compound of Formula II In a 100 mL round bottom flask, 20 mL of THF and 1.26 g of NaH (content: 70%, 36.8 mmol) wrapped with mineral oil were added, stirred to sufficiently disperse NaH, added dropwise with compound of Formula II (4.23 g, 9.2 mmol) in THF (10 mL), reacted at room temperature under vigorous agitation for 1 hour. TBDMS-Cl (tert-butyldimethylchlorosilane) (5.53 g, 36.8 mmol) was dissolved in 10 mL THF, added dropwise to the above reaction solution under stirring, the speed of dropwise adding was controlled so that the reaction temperature was not extremely high, after end of dropwise adding, the reaction was continued at room temperature under stirring for 1.5 hours. The reaction solution was poured in water, extracted with dichloromethane; the organic phase was washed with water to neutrality, washed with saturated brine, dried with anhydrous sodium sulfate. The filtrate was concentrated, separated with column chromatography, to obtain tetra (tert-butyl-dimethyl-silyl ether) of compound of Formula II.

Experimental Example 1: Test of Activity of Inhibiting HMG-CoA Reductase

1. Test Materials 1.1 Drugs
Compound of Formula II—prepared in Examples 1-4.
Standard sample of lovastatin—purchased from Sigma.
1.2 Enzymes
Rat liver microsomes (HMG-CoA reductase), could be commercially available or prepared by the following preparation method: taking out liver of male rat, washing with KESD buffer solution, centrifuging under 1200 g for 15 minutes, collecting supernatant, then centrifuging under 105,000 g twice, 90 minutes for each time, and collecting centrifugation deposit. The centrifugation deposit was added with 8.3% of glycerol, heated with 37° C. bath for 1 hour. The crude product of rat liver microsomes was purified with saturated ammonium sulfate, and 35-50% of purified fraction was collected. The purified fraction obtained could be stored in −80° C. refrigerator.
1.3 Reagents
Potassium chloride, potassium dihydrogen phosphate, ethylenediamine tetraacetic acid, dithiothreitol—purchased from Beijing Chemical Reagents Co., Ltd.;
Nicotinamide adenine dinucleotide (NADPH)—purchased from Merk;
3-hydroxy-3-methylglutary coenzyme A (HMG-CoA)—purchased from Sigma.
2. Test Methods
Compound of Formula II was dissolved in 75% ethanol solution, with initial concentration of 8.0 mg/mL, and diluted in gradient manner, to reach 4.0 mg/mL, 2.0 mg/mL, 1.0 mg/mL; lovastatin was used as positive control, dissolved with 75% ethanol solution to reach concentration of 2.0 mg/mL; in the test system, total volume was 250 μL, concentrations of ingredients were separately: potassium chloride 200 mM, potassium dihydrogen phosphate 160 mM, ethylenediamine tetraacetic acid 4 mM, dithiothreitol 10 mM, nicotinamide adenine dinucleotide and 3-hydroxy-3-methylglutary coenzyme A as two substrates separately had concentrations of: 200 μM and 50 μM, pH6.8, 30 μL of enzyme was added, 4 test groups were separately added with 10 μL of new compound solutions with different concentrations, the positive control group was added with 10 μL of lovastatin solution, the blank control group was added with 10 μL of 75% ethanol solution, and dynamitic changes of $OD_{340}$ were detected with Versamax ELISA at 37° C. condition. The rate of decline of $OD_{340}$ (expressed in slope value) as detected within 5 minutes was used to evaluate the activity of HMG-CoA reductase, and then to evaluate the activity of enzyme inhibitor and the results were shown in Table 2.
3. Test Results
The results were shown in Table 2.

TABLE 2

Test results of activity of enzyme inhibitors

| Sample name | Inhibitor concentration (mg/mL) | Inhibitor volume (μL) | Final concentration in system (μg/mL) | Slope | Inhibition rate (%) |
|---|---|---|---|---|---|
| Blank control | — | — | — | 16.0 | — |
| Lovastatin | 2.0 | 10 | 80 | 7.3 | 54.4 |
| Compound of | 8.0 | 10 | 320 | 7.5 | 53.1 |

TABLE 2-continued

Test results of activity of enzyme inhibitors

| Sample name | Inhibitor concentration (mg/mL) | Inhibitor volume (μL) | Final concentration in system (μg/mL) | Slope | Inhibition rate (%) |
|---|---|---|---|---|---|
| Formula II | 4.0 | 10 | 160 | 8.7 | 45.6 |
|  | 2.0 | 10 | 80 | 11.3 | 29.4 |
|  | 1.0 | 10 | 40 | 13.7 | 14.4 |

* Blank control was solvent; Lovastatin was positive control.

The test results showed that the compound of the present invention, especially, the compound of Formula II, had inhibition effect on activity of HMG-CoA reductase, and presented concentration-effect relationship. Its $IC_{50}$ value was about 250 μg/mL, which indicated that the compound has good inhibition effects on activity of HMG-CoA reductase.

Further studying showed that the ester derivatives or ether derivatives of compound of Formula II, for example, "tetraacetate of compound of Formula II", "tetra-p-tolylsulfonate of compound of Formula II", "tetra(trifluoromethylsulfonate) of compound of Formula II" and "tetra(tert-butyl-dimethyl-silyl ether) of compound of Formula II" as prepared in Examples 6-9 also had similar activity of inhibiting HMG-CoA reductase.

Experimental Example 2: Test of Inhibiting Cancer Cells with Compound of Formula II 1 Test Materials 1.1 Strains of Cells HCT116 and H22, purchased from Korean cell line bank, Seoul, Korea;

S180, HepG-2, YAC-1, Thp1, U937 and B16-F10, purchased from the Cell Bank of the Committee on Type Culture Collection of Chinese Academy of Sciences.

1.2 Drugs

New compound (compound of Formula II) prepared in Examples 1-4.

1.3 Reagents

MTT was purchased from Amresco; RPMI1640 and double antibody were purchased from Sigma; fetal bovine serum (FBS) was purchased from Gibco in USA; all other reagents were of analytical purity and made in China.

2 Test Methods

Cancer cells of exponential growth phase were inoculated on 96-well plate, $2 \times 10^4$ cells/well, added with drug until final drug concentrations were: 500, 250, 125, 62.5, 31.25, 15.625 and 7.8125 μg/mL, cultured at 37° C. in 5% $CO_2$ cell culture incubator for 72 hours, then added with MTT, 10 μL/well, incubated in dark at 37° C. for 4 hours, culture medium was removed, 150 μL of DMSO or acidified isopropanol was added, vibrated for 5 minutes, and then OD values were measured under wavelength of 570 nm. This was repeated for 3 times, and a blank control was set. These cell strains used the same culture medium, i.e., RPMI1640 culture medium containing 10% fetal bovine serum and 1% double antibody (penicillin and steptomycin).

Calculation Formula:

Cell survival rate=(OD value of test group/OD value of control group)×100%.

The test steps could also refer to YANG Xiuwei, et al., "Screening for antitumor activities of strychnos alkaloids in vitro", Journal of Modern Chinese Medicine, 2006, 8(9): 11-13.

3 Test Results 3.1 Activity of Compound of Formula II Against Cancer (Colon Cancer) In Vitro The results were shown in FIG. 1. The results showed that the compound of Formula II had inhibition effect on growth of human colon cancer cell strain HCT116, and exhibited concentration-effect relationship. It could be seen that this compound had potency for prophylaxis and treatment of colon cancer.

Figure 2:
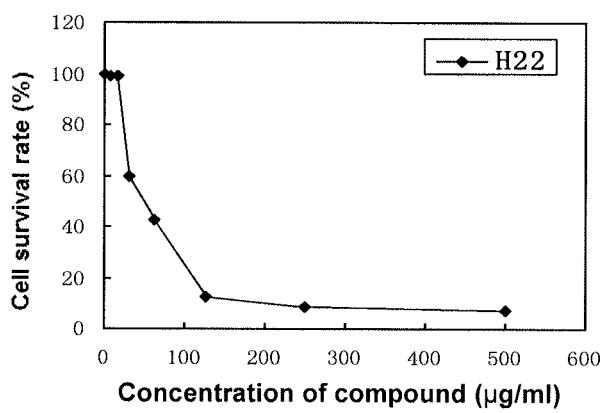
FIG. 2: inhibition curve of a compound of Formula II on growth of H22 cells.

3.2 Activity of Compound of Formula II Against Cancer (Liver Cancer) In Vitro 3.2.1 As showing in FIG. 2, the compound of Formula II had inhibition effect on growth of mice hepatoma cell line H22, and exhibited a concentration-effect relationship. Its $IC_{50}$ value was about 50 μg/mL, which suggested that this compound had good inhibition effect on proliferation of mice hepatoma cells.

Figure 3:
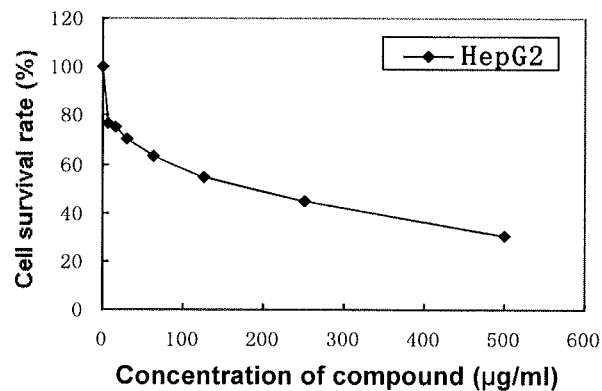
FIG. 3: inhibition curve of a compound of Formula II on growth of HepG2 cells.

3.2.2 As showing in FIG. 3, the compound of Formula II had inhibition effect on growth of human hepatoma cell line Hep22, and exhibited a concentration-effect relationship. Its $IC_{50}$ value was about 200 μg/mL, which suggested that this compound had good inhibition effect on proliferation of human hepatoma cells.

Figure 4:
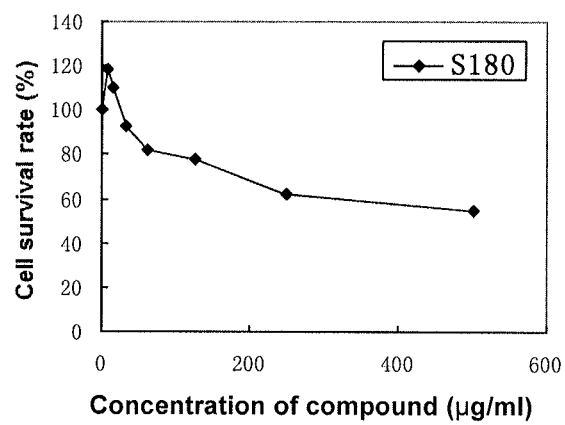
FIG. 4: inhibition curve of a compound of Formula II on growth of S180 cells.

3.2.3 As showing in FIG. 4, the compound of Formula II had inhibition effect on growth of mice sarcoma cell line S180, and exhibited a concentration-effect relationship.

It could be seen that this compound had potency for prophylaxis and treatment of liver cancer.

Figure 5:
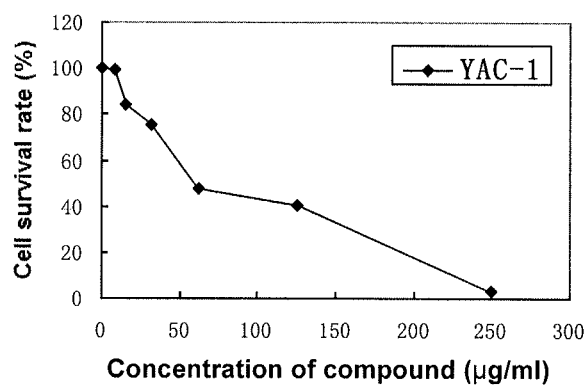
FIG. 5: inhibition curve of a compound of Formula II on growth of YAC-1 cells.

3.3 Activity of Compound of Formula II Against Cancer (Lymphoma) In Vitro 3.3.1 As showing in FIG. 5, the compound of Formula II had inhibition effect on growth of mice lymphoma cell YAC-1, and exhibited a concentration-effect relationship. Its $IC_{50}$ value was about 62.5 μg/mL, which suggested that this compound had good inhibition effect on proliferation of mice lymphoma cells.

Figure 6:
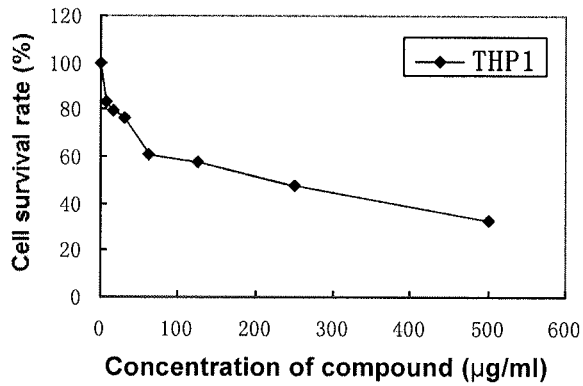
FIG. 6: inhibition curve of a compound of Formula II on growth of THP1 cells.

3.3.2 As showing in FIG. 6, the compound of Formula II had inhibition effect on growth of human mononuclear lymphoma cell THP1, and exhibited a concentration-effect relationship. Its $IC_{50}$ value was about 250 μg/mL, which suggested that this compound had good inhibition effect on proliferation of human mononuclear lymphoma cells. FIG. 6.

Figure 7:
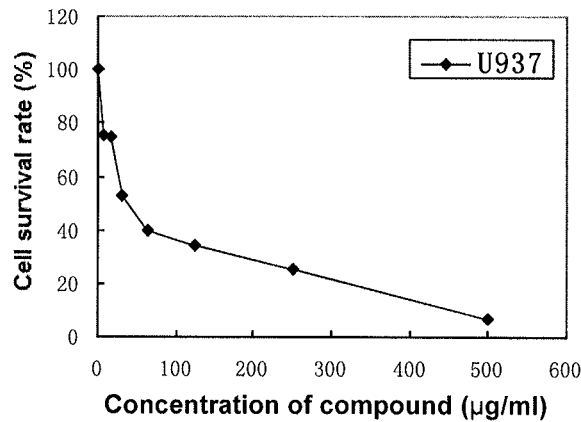
FIG. 7: inhibition curve of a compound of Formula II on growth of U937 cells.

3.3.3 As showing in FIG. 7, the compound of Formula II had inhibition effect on growth of human tissue lymphoma cell U937, and exhibited a concentration-effect relationship. Its $IC_{50}$ value was about 50 μg/mL, which suggested that this compound had good inhibition effect on proliferation of human tissue lymphoma cells.

It could be seen that this compound had potency for prophylaxis and treatment of lymph cancer (lymphoma).

3.4 Activity of Compound of Formula II Against Cancer (Melanoma) In Vitro

Figure 8:
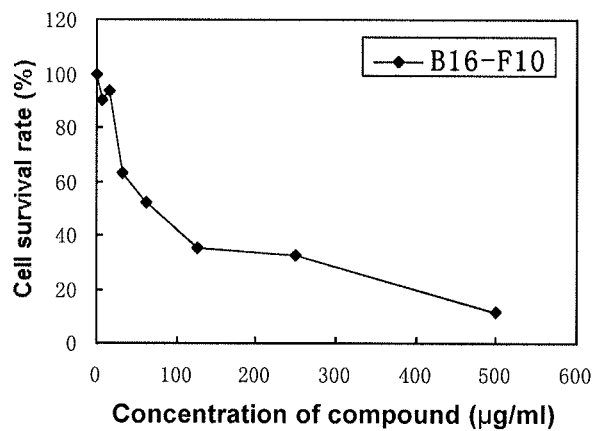
FIG. 8: inhibition curve of a compound of Formula II on growth of B16-F10 cells.

The results were shown in FIG. 8. The results showed that the compound of Formula II had inhibition effect on growth of mice melanoma cell B16-F10, and exhibited concentration-effect relationship. Its $IC_{50}$ value was about 62.5 μg/mL, which suggested that this compound had potency for prophylaxis and treatment of melanoma.

In sum, the compound of the present invention, especially compound of Formula II, had effective inhibition effects on many kinds of tumor cells, and was a potential drug for prophylaxis and/or treatment and/or adjunctive treatment of cancers.

Further studying showed that the ester derivatives or ether derivatives of compound of Formula II, for example, "tetraacetate of compound of Formula II", "tetra-p- tolylsulfonate of compound of Formula II", "tetra(trifluoromethyl sulfonate) of compound of Formula II" and "tetra(tert-butyl-dimethyl-silyl ether) of compound of Formula II" as prepared in Examples 6-9 also had similar activity of inhibiting tumor cells, and were potential drugs for prophylaxis and/or treatment and/or adjunctive treatment of cancers.

Experimental Example 3: Test of Activity of Inhibiting Lipase

1 Test Materials
1.1 Drugs
Compound of Formula II.
Orlistat—purchased from Golden Elephant Pharmacy.
1.2 Enzymes
Porcine pancreatic lipase—purchased from Sigma.
1.3 Reagents
Oleic acid—purchased from Sigma.
Toluene, olive oil, pyridine, copper acetate, $NaH_2PO_4$, $K_2HPO_4$ were all of analytic purity and made in China.
2 Test Methods
The steps were shown as follows, and could also refer to JIANG Huifang, WANG Yaqin, LIU Chunguo, Comparison and improvement of three methods for measurement of lipase activity, Journal of Chemistry & Bioengineering, 2007, 24(8):72-75; and ZHU Xiaoqing, LU Jingci, HUO Shixin, et al., Inhibitory Effect on Lipase of Alkaloid Derived from Lotus Leaf, Journal of Shanghai University (Natural Science), 2007, 13(1):85-87.
2.1 Preparation of light absorbance working curve for fatty acid: a series of oleic acid-toluene solutions with different concentrations (0-3.5 mmol/L, separately being 0, 0.225, 0.45, 0.675, 0.9, 1.125, 1.35, 1.8, 2.25, 2.7, and 3.5 mmol/L), 4 mL of each was taken and placed in conical flask, added with 1 mL of color developing agent, stirred with magnetic force for 3 minutes, oleic acid molecules and copper ions formed a green complex compound, after centrifugation, organic phase of upper layer was taken and measured at 714 nm to determine light absorbance.
2.2 Enzyme solution was 0.5 mg/mL pancreatic lipase solution; buffer solution was 0.07M $NaH_2PO_4$—$K_2HPO_4$ phosphate buffer solution (pH 7.0); color developing agent was 5% copper acetate solution, which was regulated with pyridine to have pH 6.1.
2.3 Measurement of Lipase Activity:
3 mL of 0.07M phosphate buffer solution and 1 mL of olive oil were pre-heated at a constant temperature of 37° C. for 5 minutes in water bath under agitation with a magnetic stirrer, added with 1.3 mL of enzyme solution (negative control was that without enzyme inhibitor; positive control is that added with 100 μL of 0.1 mg/mL orlistat solution; 0.6, 0.9, 1.1, 1.3, 1.8 mg/mL compound of Formula II solutions were added, each 100 μL), stirred with magnetic force for 10 minutes, immediately added with 8 mL of toluene, stirred continuously for 2 minutes, the reaction was terminated, the generated oleic acid was extracted. The solutions were transferred to centrifuge tube, centrifuged under 4000 rpm for 10 minutes, and the organic phase and water phase were layered and clarified. 4 mL of the upper layer organic phase was taken and placed in a small conical flask, added with 1 mL of color developing agent, stirred with magnetic stirrer for 3 minutes, the generated oleic acid reacted with copper ions to form green complex compound. After centrifugation under 4000 rpm for 10 minutes, the upper layer of toluene solution containing copper oleate was taken, and measured with a spectrophotometer at 714 nm to determine its light absorbance. A blank solution without lipase was prepared as control by the same method, and concentration of fatty acid could be determined by referring to light absorbance working curve of oleic acid.

3 Definition and Calculation Formula of Enzyme Activity
Enzyme activity unit of lipase was defined as follows: an enzyme amount to release 1 μmol fatty acid under certain condition was defined as 1 unit of lipase activity (U).
The following formula was used to calculate enzyme activity: $X=(cV)/(tV')$
wherein: X represents enzyme activity of lipase, U/mL; c represents concentration of fatty acid, pmol/mL; V represents volume of fatty acid solution, mL; V' represents amount of enzyme solution, mL; t represents action time, minute.

Inhibition rate=[(enzyme activity of lipase−enzyme activity of lipase after inhibition)/enzyme activity of lipase]×100%

Figure 9:
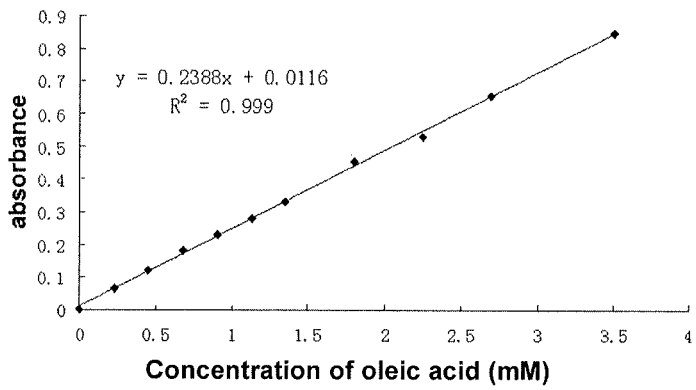
FIG. 9: absorbance working curve of oleic acid.

4 Test Results
4.1 Light Absorbance Working Curve of Oleic Acid
As shown in FIG. 9.
4.2 Test Results of Activity of Enzyme Inhibitors
As shown in following Table 3.

TABLE 3

Test results of activity of enzyme inhibitors

| Sample name | concentration of the inhibitor (mg/mL) | Final concentration of inhibitor in the system (μg/mL) | Absorbance | Concentration of generated oleic acid (mM) | Enzyme activity U/mL | Inhibition rate (%) |
|---|---|---|---|---|---|---|
| Blank control | — | — | 0.6680 | 2.75 | 1.69 | — |
| Orlistat | 0.1 | 1.85 | 0.2042 | 0.81 | 0.50 | 69.84% |
| Compound of Formula II | 6 | 111 | 0.5665 | 2.32 | 1.43 | 15.38% |
| | 9 | 166 | 0.5035 | 2.06 | 1.27 | 24.85% |
| | 11 | 203 | 0.3998 | 1.63 | 1.00 | 40.83% |
| | 13 | 240 | 0.2743 | 1.10 | 0.68 | 59.76% |
| | 18 | 333 | 0.2611 | 1.04 | 0.64 | 62.13% | wherein the enzyme activity was calculated according to the calculation formula of the above section 3, wherein:
V=8 mL; V'=1.3 mL; t=10 minutes.
The test results showed that the compound of the present invention, especially the compound of Formula II, had good inhibition effect on activity of lipase, had a $IC_{50}$ value of about 220 μg/mL, and exhibited concentration-effect relationship in inhibition effect. It could be seen that the compounds of the present invention were potential drug for prophylaxis and/or treatment and/or adjunctive treatment of obesity or diseases associated with obesity.
Further studying showed that the ester derivatives or ether derivatives of compound of Formula II, for example, "tetraacetate of compound of Formula II", "tetra-p-tolylsulfonate of compound of Formula II", "tetra(trifluoromethyl sulfonate) of compound of Formula II" and "tetra(tert-butyl-dimethyl-silyl ether) of compound of Formula II" as prepared in Examples 6-9 also had similar activity of inhibiting lipase, and were potential drugs for prophylaxis and/or treatment and/or adjunctive treatment of obesity or diseases associated with obesity.
Although the specific embodiments of the present invention have been described in details, those skilled in the art would understand these details can be modified or substituted according to the disclosed teachings, and all these changes are within the protection scope of the present invention. The whole scope of the present invention is defined by the appending claims.

What is claimed is:

1. A method for inhibiting growth of tumor cells in a subject in need thereof, the method comprising: administering to the subject a therapeutically effective amount of a compound of Formula I, or a pharmaceutically acceptable salt, ester or ether thereof,

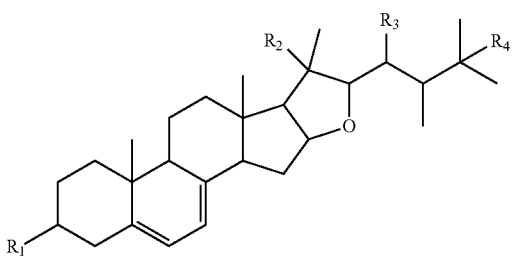

Formula (I)

wherein, $R_1$ is selected from the group consisting of —OH, =O, H, and $C_1$-$C_3$ alkyl;

$R_2$ is selected from the group consisting of —OH, H, and $C_1$-$C_3$ alkyl;

$R_3$ is selected from the group consisting of —OH, =O, H, and $C_1$-$C_3$ alkyl; and $R_4$ is selected from the group consisting of —OH, H, and $C_1$-$C_3$ alkyl wherein the tumor cells are colon cancer cells, liver cancer cells, lymph cancer cells, or melanoma cells.

2. The method of claim 1, wherein the compound is:

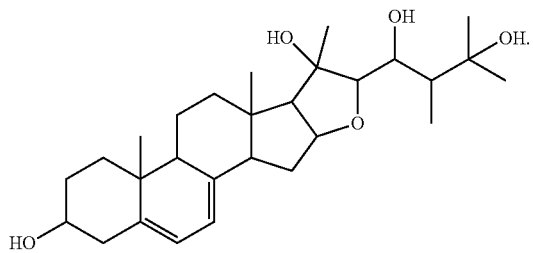 [SMILES: CC(C(O)C1OC2CC3C4=CC=C5CC(O)CCC5(C)C4CCC3(C)C2C1(C)O)C(C)(C)O]

3. The method of claim 1, wherein the compound is an ester of Formula (II):

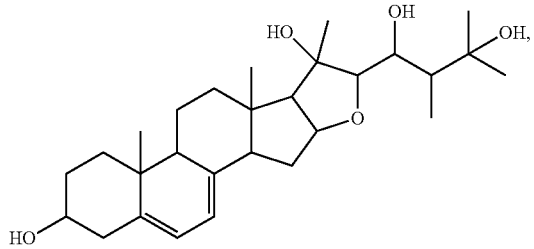

Formula (II)

wherein the ester is selected from the group consisting of formate, acetate, propionate, p-tolylsulfonate and trifluoromethylsulfonate; said ether is tert-butyl-dimethyl silyl ether.

4. The method of claim 1, wherein the compound is tetraacetate of compound of Formula II, tetra-p-tolylsulfonate of compound of Formula II, tetra(trifluoromethylsulfonate) of compound of Formula II, or tetra(tert-butyl-dimethyl-silyl ether) of compound of Formula II.

* * * * *